United States Patent
Pika et al.

(10) Patent No.: US 6,369,026 B1
(45) Date of Patent: *Apr. 9, 2002

(54) SLOW RELEASE OF FRAGRANT COMPOUNDS IN PERFUMERY USING 2-BENZOYL BENZOATES, 2-ALKANOYL BENZOATES OR ALPHA-KETO ESTERS

(75) Inventors: Jana Pika, Princeton, NJ (US); Andreas Herrmann; Christian Vial, both of Geneva (CH)

(73) Assignee: Firmenich SA, Geneve (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/635,625

(22) Filed: Aug. 10, 2000

Related U.S. Application Data

(63) Continuation of application No. 09/085,593, filed on May 28, 1998, now Pat. No. 6,133,228.

(51) Int. Cl.$^7$ .................................. A61K 7/46
(52) U.S. Cl. ..................... 512/21; 512/27; 560/37; 560/52; 560/53; 560/54
(58) Field of Search .............. 512/21, 27; 560/37, 560/52, 53, 54

(56) References Cited

U.S. PATENT DOCUMENTS

| | | | |
|---|---|---|---|
| 3,903,064 A | 9/1975 | Isigami et al. | 260/87.3 |
| 3,926,640 A | 12/1975 | Rosen | 96/115 P |
| 3,926,641 A | 12/1975 | Rosen | 96/115 P |
| 4,080,275 A | 3/1978 | Photis et al. | 204/159.23 |
| 4,180,674 A | 12/1979 | Photis | 560/52 |
| 4,781,914 A | 11/1988 | Deckner | 424/59 |
| 4,981,973 A | 1/1991 | Murray | 548/229 |
| 5,032,382 A | 7/1991 | Grollier et al. | 424/47 |
| 6,133,228 A | * 10/2000 | Pika et al. | 512/21 |

FOREIGN PATENT DOCUMENTS

JP  06-121822  5/1994

OTHER PUBLICATIONS

Klimova, E.I. et al., Chemical Abstracts, 112473d, vol. 71 (1969) 12–08 No. 23, p. 324.
Douglas C. Neckers et al. J. Org. Chem. 1997, 62, 6820–6826.
Hu, Shengkui et al., "Photochemical Reactions of Alkenyl Phenylglyoxylates," *J. Org. Chem.*, 1997, 62, 6820–6826.
Patent Abstracts of Japan vol. 18, No. 410 (C–1232), (1994) CAS RN=156521-85-6 (propanoic acid, 2–oxo, 3,7–dimethyl–6–octenyl ester * abstract.
Krause, George A., et al., "1, 5 and 1,9–Hydrogen Atom Abstractions, Photochemical Strategies for Radical Cyclizations," *J. Am. Chem. Soc.*, 1992, 114, 8705–8707.
Jones, Paul B. et al., "2–Benzoylbenzoic Acid: A Photolabile Mask for Alcohols and Thiols," *J. Org. Chem.*, 1996, 61, 9455–9461.

* cited by examiner

*Primary Examiner*—Jill Warden
*Assistant Examiner*—Monique T. Cole
(74) *Attorney, Agent, or Firm*—Winston & Strawn

(57) ABSTRACT

The present invention describes a fragrance delivery system which releases fragrant alcohols upon exposure to light. Said system comprises 2-benzoyl benzoates of general formulae

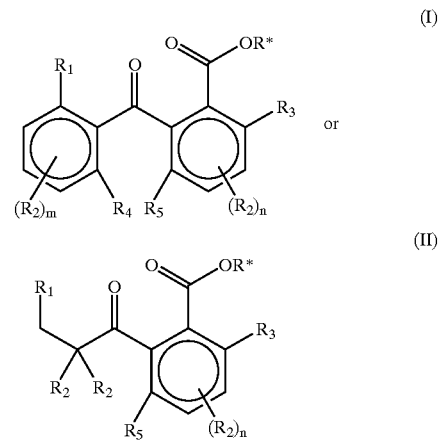

which can comprise various subtituents $R_1$–$R_5$ as defined in the application and a substituted R* which is the organic part of a fragrant alcohol.

In a further embodiment, the present invention describes a fragrance delivery system which releases fragrant aldehydes or ketones and/or fragrant compounds containing an olefin function. This system comprises α-keto esters of formula

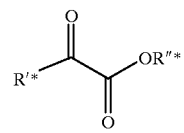

in which R'* and R"* have the meaning as defined in the application and which are generally, in case of R'*, an alkyl group carrying an abstractable hydrogen in γ-position relative to the keto function and carrying a moiety from which is derived a fragrant compound containing an olefin function, and, in case of R"*, the organic part of a primary or secondary alcohol from which is derived a fragrant aldehyde or ketone.

12 Claims, No Drawings

SLOW RELEASE OF FRAGRANT COMPOUNDS IN PERFUMERY USING 2-BENZOYL BENZOATES, 2-ALKANOYL BENZOATES OR ALPHA-KETO ESTERS

This application is a continuation of application Ser. No. 09/085,593 filed May 28, 1998 now U.S. Pat. No. 6,133,228

TECHNICAL FIELD AND PRIOR ART

The present invention relates to the field of perfumery. It relates, more particularly, to perfuming compositions or perfumed products containing a class of aliphatic or aromatic keto esters of fragrant alcohols, as defined below, which are capable of releasing said fragrant alcohol upon exposure to light, more particularly daylight. The present invention also relates to α-keto esters, as defined below, of alcohols which are precursors of fragrant aldehydes and ketones and which are capable of releasing said fragrant ketone or aldehyde upon exposure to light, more particularly daylight. Said α-keto esters may furthermore contain, in α-position to the keto group, an alkyl group which may contain various substituents and which alkyl group is derived from a fragrant molecule possessing an olefinic unsaturation. The unsaturated molecule and/or the aldehyde or ketone are released upon exposure to light, in particular daylight, of the α-keto ester.

There exists, in perfumery, a particular interest in compounds which are capable of "fixing" fragrant molecules, for example by chemical bonding or intramolecular forces like absorption, and releasing said fragrant molecules over a prolonged period of time, for example by the action of heat, enzymes, or even sunlight. Fragrant molecules have to be volatile in order to be perceived. Although many fragrant compounds are known to have good substantivity, i.e. they will cling to a surface to which they have been applied for several days and can hence be perceived over such a period of time, a great number of fragrant compounds are very volatile, and their characteristic smell can no longer be perceived after one or two days or even after several hours.

It is thus desirable to dispose of fragrance delivery systems which are capable of releasing the fragrant compound or compounds in a controlled manner, maintaining a desired smell over a prolonged period of time.

DESCRIPTION OF THE INVENTION

We have now developed a fragrance delivery system which is capable of releasing fragrant alcohols upon exposure to light, and in particular daylight. One object of the present invention is a delivery system which comprises 2-benzoyl benzoates and 2-alkanoyl benzoates of formulae

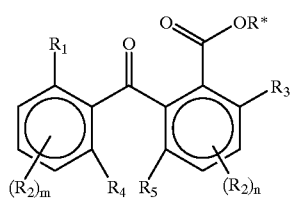

(I)

or

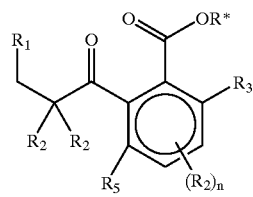

(II)

in which
R$_1$ represents hydrogen or a group of formula

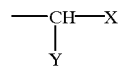

in which X and Y can be identical or different and represent, independently from each other, hydrogen, a linear or branched alkyl or alkoxy group from C$_1$ to C$_{12}$, a phenyl group which is optionally substituted, an olefinic group from C$_2$ to C$_{12}$, an alcohol group, a CO$_2$M group, a —NR$_6$R$_7$ group or a group of formula

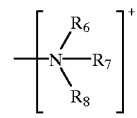

R$_2$ can be identical to R$_1$ or different from it and represents hydrogen, a linear or branched alkyl or alkoxy group from C$_1$ to C$_{12}$, a phenyl group which is optionally substituted, an olefinic group from C$_2$ to C$_{12}$, an alcohol group, a CO$_2$M group, a —NR$_6$R$_7$ group, a group of formula

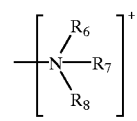

or a polyalcohol or polyether group;
R$_3$ represents hydrogen, an alkyl or alkoxy group from C$_1$ to C$_4$, linear or branched, a OH group or a NH$_2$ group;
R$_4$ and R$_5$, taken separately, have the meaning given above for R$_1$ and can be identical to or different from R$_1$ or from each other; or
R$_4$ and R$_5$, taken together, form a bridging group between the two aromatic rings, which bridging group can be a methylene or a keto group;
m is an integer from 0 to 3 and n is an integer from 0 to 2; R$_6$ and R$_7$, taken separately, each represents hydrogen, an alkyl group from C$_1$ to C$_4$, an alcohol group having an alkyl chain from C$_1$ to C$_{12}$, or a phenyl group, or, R$_6$ and R$_7$, taken together with the nitrogen atom form a 5-membered or six-membered ring possibly containing another hetero atom;
R$_8$ represents hydrogen, an alkyl group from C$_1$ to C$_4$, an alcohol group having an alkyl chain from C$_1$ to C$_{12}$ or a phenyl group;
M represents hydrogen or an alkali metal; and
R* is the organic part derived from a primary or secondary fragrant alcohol R* OH.

In the above definition, when reference is made to a fragrant alcohol, there is always meant an alcohol which not only has an odor, but which is also known to a person skilled in the art as being useful as perfuming ingredient for the formulation of perfumes or perfumed articles. The criteria a useful perfuming ingredient has to fulfil are known to a person skilled in the art and include, amongst others, a certain originality of the odoriferous note, stability and a certain price/performance ratio. Non-limiting examples for fragrant alcohols which can be used with the benzoates of the invention will be mentioned below.

The advantage of the fragrance delivery system of the present invention lies in its capacity to slowly release the fragrant alcohols R*OH from which the benzoyl benzoate esters of formula (I) or the alkanoyl benzoate esters of formula (II) are derived. The release occurs when said esters are exposed to daylight in particular. Upon absorption of energy from said light, the ester undergoes a photoreaction in the course of which the fragrant alcohol is released from the molecule into the surroundings. Said release occurs in a controlled manner, i.e. a more or less constant amount of alcohol R*OH is formed over a period of time, without an initial burst of very intense odor which becomes rapidly imperceptible as is the case with volatile alcohols. Because the release of the alcohol R*OH can occur over several days or weeks, the use of the system of the present invention obviates the drawbacks of many fragrant alcohols R*OH which are of pleasant smell but also very volatile. Good examples are citronellol and geraniol which can only be perceived over a short period of, say, one or two hours, when applied to the surface of, for example, tiles and windows in the course of a cleaning procedure using liquid cleaners; even in solution, the typical smell of said alcohols disappears within several hours. It goes without saying that the concentration of the alcohols in the application plays an important role in the time during which the fragrant molecules can be perceived.

With the system of the present invention, the typical odor of the alcohol R*OH is perceived over a much more prolonged period of time, as the 2-benzoyl benzoate or the 2-alkanoyl benzoate of the fragrance delivery system, which are not volatile, remain on the surface to which they are applied or in the solution into which they are incorporated. Upon exposure to light, the fragrant alcohol R*OH is released, and it is clear that this reaction can provide perceptible amounts of the alcohol over days or weeks, depending, amongst others, on the amount or the concentration of the fragrance delivery system, the time of exposure to light, its intensity and its wavelength.

2-Benzoyl benzoate esters of the above formula (I) which can carry various substituents in positions $R_1$, $R_2$, $R_3$, $R_4$ and $R_5$ are known to be photolabile compounds. It was suggested to use these esters as protective groups for alcohols in organic synthesis and subsequently release the alcohol present in the ester function by photolysis (see Porter et al., J. Org. Chem 1996, 61, 9455–9461). The authors conducted experiments with different alcohols, and they described the elimination of geraniol from the geranyl 2-benzoyl benzoate ($R_1=R_2=R_3=R_4=R_5=H$). However, it has not been described or suggested to use the said esters in perfumery, as a fragrance delivery system which is capable of releasing the fragrant alcohol over a prolonged period of time and thus provide a slow release fragrance effect.

As fragrant alcohol R*OH derived radical R* in the above formula (I), in principle a group derived from any fragrant alcohol which is known in the art can be used. Primary and secondary alcohols are shown to be useful in the present invention as they are liberated when exposed to daylight.

As non-limiting examples of alcohols which can be used in the present invention in the form of the 2-benzoyl benzoate esters, one can cite anisic alcohol, cinnamic alcohol, fenchylic alcohol, 9-decen-1-ol, phenethylol, citronellol, 3-methyl-5-phenyl-1-pentanol (origin: Firmenich SA, Geneva, Switzerland), Mayol® (7-p-menthan-1-ol; origin: Firmenich SA, Geneva, Switzerland), geraniol (3,7-dimethyl-2,6-octadien-1-ol), (Z)-3-hexen-1-ol, 1-hexanol, 2-hexanol, 5-ethyl-2-nonanol, 2,6-nonadien-1-ol, borneol, 1-octen-3-ol, cyclomethyl citronellol, decanol, dihydroeugenol, 8-p-menthanol, 3,7-dimethyl-1-octanol, dodecanol, eugenol, isoeugenol, Tarragol® (2-methoxy-4-propyl-1-cylohexanol; origin: Firmenich SA, Geneva, Switzerland), Polysantol® [(E)-3,3-dimethyl-5-(2',2',3'-trimethyl-3'-cyclopenten-1'-yl)-4-penten-2-ol; origin: Firmenich SA, Geneva, Switzerland] and Limbanol® [1-(2',2', 3',6'-tetramethyl-cyclohex-1-yl)-3-hexanol ; origin: Firmenich SA, Geneva, Switzerland].

It is quite obvious, however, that the process of the invention is perfectly general and can relate to many other alcohols which the skilled person is quite able to choose from the general knowledge in the art and as a function of the olfactive effect it is desired to achieve. The above list therefore is more illustrative for fragrant alcohols which are known to a person skilled in the art, and whose delivery can be improved, but it is clearly quite impossible to cite in an exhaustive manner all alcohols of formula R*OH which have a pleasant odor and the 2-benzoyl or 2-alkanoyl benzoate esters of which can be used in the fragrance delivery system of the present invention.

From the foregoing, it is evident that the fragrance delivery system is particularly appropriate for delivering fragrant alcohols R*OH which are very volatile, or which have a low perception threshold, like geraniol, citronellol or phenethylol. The benzoyl and alkanoyl benzoate esters (I) of the latter are thus preferred according to the present invention.

The chemical reaction which releases the fragrant alcohol can only occur when a source of a hydrogen radical H• is present in the fragrant delivery system. Said hydrogen radical is transferred to the oxygen of the keto-function, causing it to become reduced. Such a source can be intramolecular, i.e. the hydrogen radical comes from the 2-benzoyl benzoates of formula (I) or the 2-alkanoyl benzoates of formula (II) themselves, or intermolecular, i.e. the hydrogen radical comes from another, different source which is present in the medium in which the ester is incorporated. The intramolecular pathway or mechanism is a universal mechanism which can occur in every possible application medium, thus in the liquid or solid state. The intermolecular mechanism, however, is only possible in solution, but not in the solid state. Examples of liquid state application media are liquid air-fresheners which release the fragrant alcohol upon exposure to light. Examples of release of the fragrant alcohol in the solid state are surfaces, like those of tiles or windows, which are cleaned with a cleaner containing the fragrance delivery system of the invention, the system being thus deposited on the surface after cleaning and remaining on it as a solid film after evaporation of the liquids present in the cleaner. However, it has to be understood that the term "solid" as used beforehand is used to designate the benzoates in the neat state in which they may be a real solid, crystalline or non-crystalline, or be in the form of a more or less viscous oil.

For the 2-benzoyl benzoates of the above formula (I) or the 2-alkanoyl benzoates of the above formula (II) in which $R_1$, $R_4$ and $R_5$ are hydrogen, an external hydrogen radical source is necessary. In general, the hydrogen radical will be abstracted from the solvent in which the 2-benzoyl or the 2-alkanoyl benzoate is dissolved or provided by a solvent which is added to the solution containing the said compound. Suitable sources are known to a person skilled in the art. The most important criterion a suitable hydrogen radical source has to fulfil is that a stable radical is formed after abstraction of the hydrogen. For a given compound, and independently from other functional groups or structural elements present in the same, the presence of hydrocarbon groups which are not methyl or tert-butyl is very favorable towards the formation of a stable radical after hydrogen abstraction. Suitable groups include ethyl or n-propyl. Even better are branched secondary alkyl groups, like isopropyl or sec-butyl. It is preferred when the solvent contains an isopropyl group or is a primary or secondary alcohol. Non-limiting examples for classes of solvents are the following: aliphatic and aromatic alcohols, like methanol, ethanol, propanol, decanol or benzyl alcohol, in particular isopropanol; diols and polyols, like ethyleneglycol, glycerol, polyethyleneglycol, propyleneglycol or polypropyleneglycol; ketones, such as diisopropylketone; esters, such as isopropylacetate; aromatic solvents, such as ethylbenzene, cyclohexylbenzene or isopropylbenzene (cumene), di- or triisopropylbenzene; ethers, such as diisopropylether, tetrahydrofuran, mono-, di- or triethyleneglycoldimethylether, diethyleneglycolmonoether or polyethyleneglycoldimethylether; aminoalcohols, such as mono-, di- or triethanolamine; hydrocarbons, in particular branched hydrocarbons, including limonene.

Preferred solvents include primary and secondary alcohols, in particular isopropanol, 1-dodecanol, 2-tridecanol, butanol or amyl alcohol.

All the above-mentioned solvents can, of course, also be used for benzoyl and alkanoyl benzoate esters which react in an intramolecular pathway to release the fragrant alcohol. In such case, $R_1$, $R_4$ or $R_5$ are the intramolecular hydrogen radical source, as will be described below.

The mentioned solvents will be chosen according to their ability to release hydrogen radicals.

We have found that the intramolecular pathway for the release of the fragrant alcohol only occurs when at least one of the groups $R_1$, $R_4$ or $R_5$ of formula (I) or (II), which is in 2-position relative to the keto function, is a group of formula

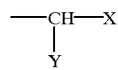

from which the hydrogen radical is easily transferred to the keto function, due to the vicinity of the group $R_1$ to the keto function by which an energetically favorable transition state is possible. X and Y are chosen to stabilize the resulting radical

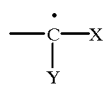

which remains after abstraction of the hydrogen radical and its transfer to the keto function. Suitable groups X and Y which can stabilize radicals are known to a person skilled in the art, and X and Y, which can be the same or different, will be chosen according to the respective benzoyl benzoate and the fragrant alcohol R*OH used in a given fragrance delivery system in order to give the best results, i.e. the desired release rate for the fragrant alcohol. Preferably X and Y are, independently from each other, a group as defined above with respect to formulae (I) and (II).

The compounds of formula (I) can contain, in addition to the substituent $R_1$ in 2-position of the cycle relative to the keto function, a further substituent $R_4$ in 6-position. It is evident that this substituent $R_4$ can also function as a hydrogen radical source, after a rotation around the single bond between the keto function and the phenyl ring. Moreover, the same applies to the group $R_5$ of the above formula (I) or (II), which is optionally present in the phenyl ring which carries the ester function. $R_5$, after a rotation of the phenyl group, can also serve as a hydrogen radical source. $R_4$ and $R_5$ thus have the same meaning as $R_1$, which has been defined above, and $R_4$ and $R_5$ can be identical to $R_1$, or they can be different from $R_1$ and, respectively, from each other.

The two phenyl groups of the 2-benzoyl benzoates or formula (I) can furthermore be bridged by a methylene or keto group.

We have furthermore found that it can be advantageous with respect to the release of the fragrant alcohol when the respective benzoyl benzoate of formula (I) or the respective alkanoyl benzoate of formula (II) carries a substituent $R_3$ other than hydrogen in the ortho-position to the —COOR*—function. The purpose of this substituent is to establish a favorable conformation of the —COOR*— function relative to the keto group, or respectively to the reduced keto-group, in order to facilitate the cyclization to the lactone which occurs after release of the alcohol. This reaction leads to the release of the fragrant alcohol R*OH. Practically, any group which is inert towards the —COOR*—function can be used, and they are known to a person skilled in the art. The groups defined in the above formula (I) and (II), namely linear or branched alkyl or alkoxy from $C_1$ to $C_4$, OH or $NH_2$ have revealed themselves as being appropriate from the point of view of effectiveness, and, of course, synthetic access.

The benzoyl benzoates of formula (I) and the alkanoyl benzoate of formula (II) can furthermore carry one or more substituents $R_2$ in the positions indicated and defined above. Substituents $R_2$, however, seem to be of less importance to the reactivity and the performance of the fragrance delivery system of the present invention, although it is often preferred, for reasons of easy accessibility of the corresponding 2-benzoyl and 2-alkanoyl benzoates of the invention, to use an ester wherein $R_2$ is a group other than hydrogen. It is however possible to adapt e.g. the stability of the 2-benzoyl and 2-alkanoyl benzoates of the present invention to the respective application desired. The 2-benzoyl benzoates can e.g. be rendered more hydrophilic by one or more groups $R_2$ which are a quaternary amine group, a polyalcohol group or a polyether group. Specific examples for said functional groups are known to a person skilled in the art, and the groups will be chosen according to the effect desired.

Preferred 2-benzoyl benzoate esters of the present invention are those of formula

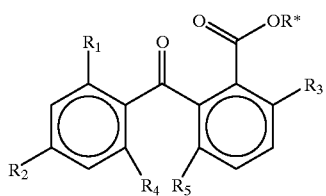

(I')

in which $R_1$ is a branched alkyl group from $C_3$ to $C_4$ containing a secondary hydrocarbon group;

R$_2$ is a branched alkyl group from C$_3$ to C$_4$ and is identical to R$_1$;

R$_3$ is hydrogen or a linear or branched alkyl group from C$_1$ to C$_4$;

R$_4$ is hydrogen or a linear or branched alkyl group from C$_1$ to C$_4$;

R$_5$ is hydrogen or a linear or branched alkyl group from C$_1$ to C$_4$;

R* is the organic part derived from a primary or secondary fragrant alcohol R*OH.

Generally, with respect to the above formulae (I) and (I'), it can be said that it is preferred when R$_1$, R$_4$ or R$_5$ which are responsible for the transfer of the hydrogen radical towards the keto function, is an isopropyl group, irrespective of the other substituents which may be present in the molecule. The isopropyl group was found to be the substituent which is most easily available, from a synthetic point of view, and which readily transfers hydrogen to the keto function, which we attribute to its ability to form a stable radical after abstraction of hydrogen.

The most preferred compounds according to the above formula (I') are geranyl 2-(2'-isopropylbenzoyl)benzoate, geranyl 2-(2',4'-diisopropyl-benzoyl)benzoate and 3,3-dimethyl-5-(2',2',3'-trimethyl-3'-cyclopenten-1'-yl)-4-penten-2-yl 2-(2',4'-diisopropylbenzoyl)benzoate [(E)-3,3-dimethyl-5-(2',2',3'-trimethyl-3'-cyclopenten-1'-yl)-4-penten-2-ol is a secondary alcohol sold under the name Polysantol® by Firmenich SA, Geneva, Switzerland].

The 2-benzoyl and 2-alkanoyl benzoates of the present invention are synthesized by esterification of the respective 2-benzoyl and 2-alkanoyl benzoic acids with the desired alcohol, in a way known to a person skilled in the art, preferably using 4-dimethylaminopyridine in pyridine and 1,3-dicyclohexylcarbodiimide. The above-mentioned benzoic acids are obtained from the respective phthalic anhydride. This latter is brought to reaction, for example, with the desired substituted or unsubstituted benzene in a Friedel-Crafts reaction. If necessary, the respective phthalic anhydride can also be reacted with the Grignard reagent, the organolithium compound or another appropriate organometallic compound of the desired substituted or unsubstituted benzene or alkane, respectively.

A further object of the present invention is a fragrance delivery system comprising α-keto esters of formula

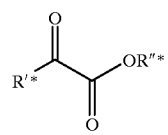

(III)

in which

R'* is hydrogen or a linear or branched, unsubstituted or substituted alkyl group from C$_1$ to C$_{35}$, an unsubstituted or substituted cycloalkyl group from C$_5$ to C$_6$, an unsubstituted or substituted phenyl or naphthyl group, or an alkyl group carrying an abstractable hydrogen in γ-position relative to the α-keto function and comprising a moiety from which is derived a fragrant compound containing an olefin function, such that said fragrant compound containing an olefin function is eliminated after abstraction of said γ-hydrogen atom;

R"* is hydrogen or a methyl, ethyl or tert-butyl group or is the organic part of a primary or secondary alcohol from which is derived a fragrant aldehyde or ketone, at least one of the groups R'* and R"* being a group which is derived from a fragrant compound.

In the above definition, when reference is made to a fragrant compound, aldehyde or ketone, it is always meant a compound which not only has an odor, but which is also known to a person skilled in the art as being useful as a perfuming ingredient for the formulation of perfumes or perfumed articles. The criteria a useful perfuming ingredient has to fulfil are known to a person skilled in the art and include, amongst others, a certain originality of the odoriferous note, stability and a certain price/performance ratio. Non-limiting examples for fragrant compounds which can be used with the α-keto esters of the invention will be mentioned below.

Like the above-described 2-benzoyl benzoates and 2-alkanoyl benzoates, the α-keto esters of the above formula (III) release fragrant compounds upon exposure to light, in particular daylight. The α-keto esters of formula (III), however, are capable of eliminating, i.e. releasing, either a fragrant compound containing an olefin function from the group R'* in 1-position relative to the keto function, or a fragrant aldehyde or ketone which is derived from the alcohol R"*OH from which the organic part R"* is present in the ester function of the keto esters of the present invention.

The release of the fragrant compound from the keto esters occurs after an intramolecular transfer of an abstractable hydrogen radical, in γ-position to the α-keto function, to said keto function. The respective part of the molecule from which the hydrogen radical has been abstracted is subsequently released from the reduced keto ester, with concomitant formation of a double bond. The above is illustrated in the scheme below in which possible substituents in the respective parts of the molecules have been omitted for reasons of clarity. The double bonds which will be formed after elimination are indicated by dotted lines.

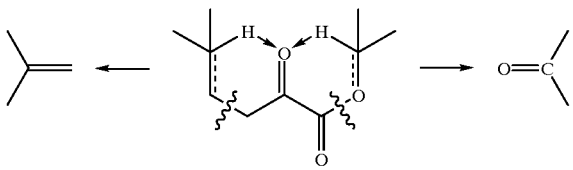

It is to be understood that the α-keto esters of the present invention can release only one molecule of fragrant compound per molecule of α-keto ester. However, when the hydrogen transfer to the α-keto function is able to occur from the one or the other side of said function, as illustrated above, a certain part of the molecules will release a ketone or aldehyde and a certain part will release the olefin compound. The proportions of the two products released depend on the relative rate of each hydrogen transfer reaction. According to the effect desired, the α-keto esters of the invention can be tailored to release exclusively a fragrant ketone or aldehyde, or exclusively a fragrant compound containing an olefin group, or both. When only one of the two classes of fragrant compounds is to be released from the α-keto esters of the invention, the part of the molecule from which no release shall occur does not contain an abstractable hydrogen atom in γ-position to the keto function, i.e. either no hydrogen atom at all is present in the said position, or it is one which is not abstracted.

It is evident that a fragrance delivery system which contains the α-keto esters of the above formula (III) has all the advantages described above for the 2-benzoyl and 2-alkanoyl benzoates of formula (1) and (II), i.e. the release of the fragrant compound occurs in a more or less constant amount. No initial burst of very intensive odor which becomes imperceptible after a relatively short period of time occurs, as is often observed with volatile aldehydes or ketones or fragrant compounds containing an olefin group. With the α-keto esters of the present invention, such disadvantages are obviated because the esters will remain on a surface to which they have been applied or in the solution into which they have been incorporated. Upon exposure to light, the fragrant compound or compounds are released, and this reaction can provide perceptible amounts of the compound over days or weeks, depending, amongst others, on the amount or the concentration of the α-keto esters, the time of exposure to light and its intensity.

Additionally, the α-keto esters of the present invention allow for the generation of mixtures of two different fragrant compounds, and in different proportions, if desired.

In principle, any fragrant aldehyde or ketone which is known in the art can be released from the α-keto esters of the invention in which they are chemically bound in the form of the ester of their corresponding secondary or primary alcohol.

Non-limiting examples for fragrant aldehydes which can be released from the α-keto esters include saturated and unsaturated aldehydes from $C_6$ to $C_{13}$, citral, citronellal, campholenic aldehyde, cinnamic aldehyde, hexylcinnamic aldehyde, formyl pinane, hydroxycitronellal, cuminic aldehyde, vanillin, ethylvanillin, Lilial® [3-(4-tert-butylphenyl)-2-methylpropanal; origin: Givandan-Roure SA, Vernier, Switzerland], Lyral® [4- and 3-(4-hydroxy-4-methylpentyl)-3-cyclohexene-1-carbaldehyde; origin: International Flavors and Fragrances, USA], Bourgeonal® [3-(4-tert-butylphenyl)propanal; origin: Quest International, Naarden, Netherlands], heliopropanal [3-(1,3-benzodioxol-5-yl)-2-methylpropanal; origin: Firmenich SA, Geneva, Switzerland], Zestover (2,4-dimethyl-3-cyclohexene-1-carbaldehyde; origin: Firmenich SA, Geneva, Switzerland), Trifernal® (3-phenylbutanal; origin: Firmenich SA, Geneva, Switzerland) and α-sinensal.

Non-limiting examples for ketones which can be released from the α-keto esters include camphor, carvone, menthone, ionones, irones, damascenones and damacones, 4-(4-hydroxy-1-phenyl)-2-butanone (raspberry ketone) and Hedione® (methyl dihydrojasmonate; origin: Firmenich SA, Geneva, Switzerland).

With respect to the fragrant compounds carrying an olefin group, in principle any compound containing such olefin group and, in addition, any osmophoric group known in perfumery can be used. As non-limiting examples for osmophoric groups, one can cite alcohol, ether, ester, aldehyde and keto groups, the thio analogues of the said groups, nitrile, nitro and olefin groups.

As non-limiting examples for fragrant compounds which carry an olefin group, there can be cited linalool, 1,3,5-undecatrienes, myrcene, myrcenol, dihydromyrcenol, nerolidol, sinensals, limonene, carvone and farnesenes.

It is quite obvious, however, that the invention is perfectly general and can relate to many other aldehydes, ketones and olefins which are useful as fragrant compounds. The person skilled in the art is quite able to choose these compounds from the general knowledge in the art and from the olfactive effect it is desired to achieve. The above list is therefore more illustrative for the compounds which are known to a person skilled in the art, and whose delivery can be improved. It is clearly quite impossible to cite in an exhaustive manner all aldehydes, ketones and olefins which have a pleasant odor and which can be used in the form of derivatives in the α-keto esters of formula (III) from which they are released upon exposure to light.

The α-keto esters of the present invention are in particular appropriate for delivering fragrant aldehydes and ketones and fragrant compounds containing an olefin group which are very volatile or which have a low perception threshold. Preferred aldehydes and ketones include citronellal, citral, hydroxycitronellal, Hedione®, raspberry ketone and aldehydes from $C_6$ to $C_{13}$, saturated or unsaturated. Preferred fragrant compound containing an olefin group include linalool, myrcene and myrcenol.

In case the α-keto esters of the present invention are used to release exclusively aldehydes or ketones, the group R'* is hydrogen, phenyl, cyclohexyl or cyclopentyl, methyl, ethyl, n-propyl, isopropyl, sec-butyl, isobutyl or tert-butyl, i.e. groups which do not provide an abstractable hydrogen atom in γ-position to the α-keto function or which do not form a stable radical when a hydrogen radical is abstracted from them. In the latter case, small amounts of olefin may be formed which however do not interfere with the aldehyde or ketone released.

Likewise, when the α-keto esters of the present invention are used to release a fragrant compound containing an olefin group only, then the group R"* will be hydrogen or a methyl, ethyl or tert-butyl group, thus a group which does not provide an abstractable proton in γ-position to the α-keto function or which do not form a stable radical when a hydrogen radical is abstracted from them.

It is preferred when the fragrance delivery system of the present invention contains α-keto esters of formula (III) in which R"* is the organic part of a primary or secondary alcohol from which is derived a fragrant aldehyde or ketone and in which R'* is phenyl, cyclohexyl or an alkyl group from $C_1$ to $C_4$.

As is clear from the above, the α-keto esters of formula (III) always react, before releasing a fragrant compound, in an intramolecular hydrogen abstraction reaction. A fragrance delivery system containing the α-keto esters of formula (III) therefore in no case needs an external hydrogen radical source, contrary to the 2-benzoyl and 2-alkanoyl benzoates of formulae (I) and (II) from which some compounds react under abstraction of a hydrogen radical from the solvent. A fragrance delivery system containing α-keto esters of the present invention may thus comprise a solvent the choice of which is not supposed to be critical. Suitable classes of solvents include alcohols, ethers, esters, ketones, amines and aminoalcohols.

The α-keto esters of formula (III) can be prepared, on one hand, by esterification of the respective α-ketoacids with the primary or secondary alcohols which are the precursors of the fragrant aldehydes and ketones to be releasead. Another way for the preparation of the α-keto esters of the present invention is the reaction of the bis(oxalyl) ester of the primary or secondary precursor alcohol R"*OH with the Grignard compound of the appropriate group R'* as defined in formula(III). The reaction is illustrated in the scheme below.

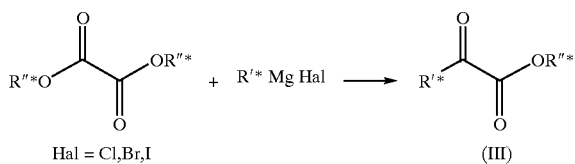

Hal = Cl,Br,I                         (III)

The bis(oxalyl) ester is prepared from oxalyl chloride and the desired alcohol, see Syn. Commun. 1981, 943.

Various α-keto esters of formula (III) in which R'* is phenyl and R"* is the alcohol precursor of a fragrant aldehyde are described in the literature. Also described is hexyl (cyclohexyl)oxoacetate (see DE-OS 29 09 951 to Bayer AG, describing the use of the said compound as starting product for the synthesis of catalysts for the polymerisation of olefins), which would release n-hexanal upon irridiation.

The release of the above-mentioned fragrant compounds from the delivery system occurs upon the exposure to light, e.g. the normal daylight which can penetrate through ordinary windows in houses and which is not particularly rich in UV-radiation. It goes without saying that upon exposure to bright sunlight, in particular outdoors, the release of the fragrant alcohol, aldehyde, ketone or alkene will occur faster and to a greater extent than upon exposure to the light in a room inside a building. Of course, the reaction which releases the fragrant compound from the delivery system can also be initiated by an appropriate artificial lamp.

The fragrance delivery systems of the present invention can be used in any application in which a prolonged, defined release of the above-mentioned fragrant compounds is desired. They therefore mostly find use in functional perfumery, in articles which are exposed to daylight when in use or which are applied to other articles which thereafter are exposed to daylight. Suitable examples include air-fresheners in liquid and solid form which, with the delivery system of the present invention, still can release a fragrance when conventional air-fresheners, i.e. those not containing the system of the present invention, are exhausted. Other examples are window and household cleaners, all purpose-cleaners and furniture polish. The surfaces which have been cleaned with such cleaners will diffuse the smell of the perfume much longer than when cleaned with conventional cleaners. Detergents and fabric softeners can also contain the delivery system of the present invention, and the clothes washed or treated with such detergents or softeners will diffuse the fragrant compound even after having been stored in the wardrobe for weeks or months.

The release of the fragrant compound occurs in all the above-mentioned application examples. All possible types of window, household, all-purpose cleaners, air-fresheners, detergents and fabric softeners can be used with the fragrance delivery system of the present invention, which has revealed itself to be useful in all types of these above-mentioned application examples.

It can be said that generally all products which can be applied to a surface which is exposable to light may contain the system of the present invention. Examples include surfaces which belong to the human body, like skin or hair, surfaces in buildings and apartments, like floors, windows, tiles or furniture, or surfaces of clothes. It is clear that the system of the invention can also be used to release fragrances from liquids, like in liquid air-fresheners. The possible applications of this type, however, appear to be less general than the application on the various surfaces mentioned.

Of course, the above examples are only illustrative and non-limiting as referring to preferred embodiments. All other current articles in functional and fine perfumery may contain the system of the present invention, and these articles include soaps, bath or shower gels, shampoos, hairsprays or other hair care products, cosmetic preparations, body deodorants, and even perfumes or colognes.

In the above-cited applications, the device of the present invention can be used alone or with other perfuming ingredients, solvents and adjuvants of current use in the art. The nature and variety of these co-ingredients does not require a detailed description which, moreover could not be exhaustive, and a person skilled in the art will be able to choose said coingredients by his general knowledge and in function of the nature of the product to be perfumed and the olfactive effect sought. These perfuming ingredients belong to such varied chemical classes as alcohols, aldehydes, ketones, esters, ethers, acetates, nitrites, terpene hydrocarbons, nitrogen- or sulfur-containing heterocyclic compounds, as well as essential oils of natural or synthetic origin. By way of example, embodiments of compounds can be found in standard reference works, such as the book of S. Arctander, Perfume and Flavor Chemicals, 1969, Montclair, N.J., USA, or more recent versions thereof, or in other works of similar nature.

The proportions in which the system of the present invention can be incorporated in the various above-mentioned products vary within a wide range of values. These values depend on the nature of the fragrant compound to be released, the nature of the article or product which is to be perfumed and the desired olfactive effect, as well as on the nature of the co-ingredients in a given composition when the system of the present invention is used in admixture with perfuming co-ingredients, solvents or adjuvants of current use in the art.

By way of example, one can cite typical concentrations of the order of 0.01 to 5%, or even 10% by weight relative to the weight of the consumer products cited above into which it is incorporated. Higher concentrations than those mentioned above can be used when the system is applied in perfuming compositions, perfumes or colognes.

The invention will now be described in greater detail in the following examples in which the temperatures are indicated in degrees centigrade and the abbreviations have the usual meaning in the art.

EMBODIMENTS OF THE INVENTION

General

The following chemicals were obtained from commercial sources geraniol, Polysantol®, 2-benzoylbenzoate, dicyclohexylcarbodiimide (DCC), diisopropyl-carbodiimide (DIC), 4-dimethylamino-pyridine, magnesium turnings, 2-iodoisopropyl benzene, 1,3-diisopropylbenzene, $AlCl_3$, 1,2-dichloroethane, 1,2-dibromoethane, citronellol, oxalyl chloride, 3-methyl-2-oxo-pentanoic acid, bromocyclohexane, bromobenzene, 2-oxo-pentanoic acid, 4-bromo acetophenone, ethylene glycol, 2-bromo-tetradecane, 1-bromo-tetradecane.

Geranyl 2-benzoylbenzoate (1) was prepared as described by Porter et al., J. Org, Chem. 1996, 61, 9455–9461.

A. Execution of Photorelease Assays and Analysis for 2-Benzoyl Benzoates and 2-Alkanoyl Benzoates Photorelease Assays Photorelease assays were conducted on solutions (typical concentrations=0.005 to 0.01 M) or films of the respective esters in 10 mL borosilicate glass volumetric flasks (Pyrex®) unless otherwise stated. The films were prepared by dissolving the ester in a small (<1 mL) volume of pentane or acetone, transferring to a 10 mL volumetric flask and drying under a stream of nitrogen or reduced pressure while rotating the flask to evenly disperse the ester on the surface of the glass. The samples were not degassed.

The Fadeometer assays were done using an Atlas Ci35 Fadeometer, equipped with a borosilicate glass inner filter and a soda lime outer filter, set at 0.35 W/m$^2$ at 340 nm.

Natural light assays were done by putting the samples in a metal rack outdoors during daylight hours. Natural light conditions could also be mimicked by using a 8 W 366 nm UV lamp with an intensity of 500 $\mu$W/cm$^2$ (VWR Scientific Products).

Analysis

After photolysis, the quantity of alcohol released was measured by GC analysis of duplicate samples using the alcohol as the external standard. The presence of photoreleased alcohol was checked using GC retention times, GC-MS and also by smelling the samples. The ester solutions were injected neat while the solid films were dissolved and diluted volumetrically to 10 mL in acetone. Samples (1 $\mu$L, split 54:1, injector at 250° C.) were injected as acetone solutions. Gas chromatography-flame ionization detection (GC-FID) was carried out using an SPB-1 capillary column (30 m, 250 $\mu$m id, 0,25 $\mu$m film, He carrier gas, 1.0 mL/min).

Gas chromatography-mass spectrometry (GC-MS) was performed using an HP-5890 GC coupled to an HP 5989A mass spectrometer. The GC separation utilized an SPB-1 capillary column (30 m, 0,25 $\mu$m id, 0.25 $\mu$m film, He carrier gas, 1 mL/min). An SPB-1 column (30 m, 0,32 $\mu$m id, 0.25 $\mu$m film, He carrier gas, 1.3 mL/min) was used for the GC separation with the same temperature program used for the GC-MS. The samples (1 $\mu$L, split 16:1, injector at 250° C.) were injected as acetone solutions.

B. Execution of Photorelease Assays and Analysis for α-keto Esters

Photorelease Assays

Photorelease assays were conducted on solutions or on films of the respective ester and will be described below in each of the examples referring to the respective mode of irradiation.

All samples were irradiated using a xenon lamp (Heraeus Sundest CPS at 460W/m2) or a UV lamp (UVP Model UVL-28, 8W at 360 nm) for 3–3.5 h, as will be indicated for each sample in the respective examples.

Analysis

The mode of analysis for each sample which had been irradiated will be indicated in each respective example.

Analytical HPLC was carried out on a Spectra Physics instrument composed from a SP 8800 ternary pump, a SP 5750 injection valve, a SP 8780 autosampler, a Waters 490E UV detector and a Spectra Physics ChromJet integrator Macherey-Nagel Nucleosil 5 $C_{18}$ reversed phase column (125×4 mm i.d.) eluted with a gradient from acetonitrile/water 1:1 to pure acetonitrile during 20 min. The injection volume was 50 $\mu$l and the UV detector wavelength fixed at 220 nm.

Analytical GC The on-column injections were carried out on a Carlo Erba MFC 500 using a precolumn (30 cm) and a Suppelco SPB-1 capillary column (30 m) at 115° C. for 8 min, then to 280° C., helium pressure 75 kPa, injection volume 2 $\mu$l. All other GC analyses were carried out on the same instrument equiped with a Fisons AS 800 autosampler using a J&W Scientific DB1 capillary column (15 m) at 70 or 80° C. for 10 min, then to 260° C., helium pressure 50 kPa, injection volume 0.5 $\mu$l.

EXAMPLE 1

Preparation of Substituted 2-Benzoyl Benzoates a) Geranyl 2-(2'-isopropylbenzoyl)benzoate (2)

Magnesium (0.46 g, 19 mmol) and a crystal of iodine were placed in a dry round bottom flask which was heated to activate the magnesium. Diethyl ether was added to cover the magnesium (50 mL) and several drops of 2-iodoisopropyl benzene in diethyl ether were added to start the preparation of the Grignard reagent. When the latter was underway, a solution of 2-iodoisopropyl benzene (4.18 g, 17 mmol) in diethyl ether (20 mL) was added over 20 minutes. The reaction mixture was stirred for another 15 minutes and then refluxed for 20 minutes. Phthalic anhydride (3.11 g, 21 mmol) in toluene (50 mL) was added dropwise to the Grignard reagent at room temperature. The reaction temperature was raised to 60° C. and the diethyl ether removed by evaporation.

The reaction was allowed to stir at 60° C. for 6 hours. The reaction mixture was poured on ice and 10% HCl (100 mL) and extracted twice with diethyl ether. The organic phase was washed twice with a 10% $Na_2CO_3$ solution (200 mL). The aqueous phase was acidified with acetic acid (120 mL) and extracted twice with diethyl ether (200 mL). The organic phase was washed three times with $NaHCO_3$ (100 mL) and then twice with water. The ether phase was dried over $Na_2SO_4$, filtered and concentrated.

The yield was 1.43 g (purity: 94.6%, isolated yield: 31%) of 2-(2-isopropylbenzoyl)benzoic acid.

For esterification, a solution of the thus obtained acid (3.77 g, 10 mmol), geraniol (1.4 g, 9 mmol) and 4-dimethylaminopyridine (DMAP, 0.244 g, 2mmol) in pyridine (15 mL) was prepared under anhydrous conditions. 1,3-Dicyclohexylcarbodiimide (DCC, 2.06 g, 10 mmol) was added and the reaction was stirred under a stream of nitrogen gas for 52 hours. The reaction mixture was partitioned between 1M HCl and ethyl acetate.

The organic extract was dried over $Na_2SO_4$, filtered and concentrated under vacuum.

The ester product was purified by flash column chromatography ($SiO_2$, 7:1 cyclohexane:ethyl acetate; isolated yield: 0.7 g, 48%) to give the following analytical data:

UV (cyclohexane) 240 ($\epsilon$ 13 000), 280 ($\epsilon$ 5 000); $^1$H-NMR (360 MHz, $CDCl_3$) δ (ppm): 7.85 (m, 1H); 7.49 (m, 4H); 7.38 (m, 1H); 7.23 (dd, 1H, J=1, 8 Hz); 7.12 (m, 1H); 5.21 (1H, m); 5.05 (1H, m); 4.65 (1H d, J=7 Hz); 3.70 (1H, m); 2.00 (4H, m); 1.66 (3H, brs); 1.63 (3H, brs); 1.58 (3H, br s); 1.28 (6H, d, J=7 Hz) $^{13}$CNMR(90 MHz, $CDCl_3$) δ (ppm): 198.7(s), 167.2(s), 150.1(s), 142.5(s), 142.1(s), 136.7(s), 131.6(d), 131.1(d), 130.6(d), 130.3(d), 129.5(d), 129.0(d), 126.4(d), 124.9(d), 123.8(d), 117.8(d), 62.4(t), 39.5(t), 29.3(d), 26.3(t), 24.1(q), 17.7(q), 16.5(q).

b) Geranyl 2-(2',4'-diisopropylbenzoyl)benzoate (3)

Phthalic anhydride (19.3 g, 0.13 mol) was placed in a flame-dried three-neck round-bottom flask under nitrogen. 1,2-Dibromoethane (100 mL) and aluminum chloride (36.0 g, 0.27 mol) were added. The reaction solution was stirred at room temperature while 1,3-diisopropylbenzene (20.4 g, 0.126 mol) was added dropwise over the space of an hour. The reaction mixture was stirred at 100 ° C. for two hours. Upon completion, the reaction mixture was cooled to room temperature and poured over ice/hydrochloric acid (1:1). The solution was extracted twice with dichloromethane.

The organic extract was washed with saturated aqueous sodium chloride solution to neutrality, dried over anhydrous sodium sulfate, filtered and concentrated under vacuum to yield a heavy brown oil of 80% purity (isolated yield=36 g, % yield=74%). The thus obtained 2-(2',4'- diisopropylbenzoyl)benzoic acid showed the following analytical characteristics

IR: (neat), 2965, 1695, 1670, 1605 cm$^{-1}$, $^1$H NMR (360 MHz, CDCl$_3$) δ ppm: 7.98 (1H, dd, J=1, 8 Hz), 7.59 (1H, m), 7.52 (1H,m),7.37(1H, dd, J=1, 8 Hz),7.31 (1H, d, J=1.2 Hz),7.09(1H, d, J=8 Hz),6.94 (1H, dd, J=2,8 Hz), 3.82 (1H, m), 2.91 (1H, m), 1.25 (12H, m); $^{13}$C NMR (90 MHz, CDCl$_{13}$) δ ppm: 198.6 (s), 170.9 (s), 153.2 (s), 151.0 (s), 143.8 (s), 133.9 (s), 132.3 (d), 131.7 (d), 130.6 (d), 129.8 (d), 128.9 (s), 128.7 (d), 125.0 (d), 122.7 (d), 34.3 (d), 29.0 (d), 24.1 (q), 24.1 (q), 23.7 (q), 23.7 (q); LREIMS: m/z (relative abundance) 310 (5, M$^+$), 265 (43), 249 (45), 221 (100), 149 (32), 84 (41), 49 (35).

The thus obtained product (1.15 g, 3.7 mmol) was dissolved in dry pyridine (10 mL) in a flame-dried three-neck round-bottom flask. To the solution were added geraniol (freshly distilled, 0.55 g, 3.6 mmol), 4-dimethylaminopyridine (DMAP, 0,10 g, 0.8 mmol) and 1,3-dicyclohexylcarbodiimide (DCC, 0.76 g, 3.7 mmol). The reaction mixture was stirred at room temperature overnight. When complete, the reaction mixture was poured onto shaved ice (20 g), 32% hydrochloric acid (24 g) and ethyl acetate (30 mL) and stirred vigorously for 10 minutes. The solution was extracted twice with diethyl ether and the organic phase was washed twice with saturated aqueous sodium bicarbonate solution and twice with water. The organic phase was dried over anhydrous sodium sulfate and concentrated under vacuum. The product was purified by redissolving in pentane, crystallizing at 4° C., and filtering through Celite. The filtered solution was concentrated under vacuum and purified further by normal phase silica gel chromatography (20% diethyl ether/heptane). Geranyl 2-(2'-4'-diisopropylbenzoyl)benzoate was isolated as a pale yellow oil (isolated yield=1.08 g, % yield=74.5%), having the following analytical data: $^1$H NMR (360 MHz, CDCl$_3$) δ ppm: 7.76 (1H, dd, J=3, 6 Hz), 7.51 (2H, m), 7.37 (1H, dd, J=3, 6 Hz),7.31 (1H, d, J=2 Hz),7.18(1H, d, J=8 Hz), 6.97(1H, dd, J=2, 8 Hz), 5.22 (1H, m), 5.04 (1H, m), 4.64 (2H, d, J=7 Hz), 3.79 (1H, m), 2.92 (1H, m), 2.1–1.9 (4H, m), 1.74 (3H, br s), 1.62 (3H, br s), 1.58 (3H, br s), 1.28 (6H, d, J=7 Hz), 1.25 (6H, d, J=7 Hz); $^{13}$C NMR (90 MHz, CDCl$_3$) δ ppm: 198.5 (s), 167.2 (s), 152.9 (s), 150.6 (s), 142.7(s), 142.4 (s), 134.1 (s), 131.7 (s), 131.2(s), 131.6 (d), 131.1 (d), 129.9 (d), 129.6 (d), 128.7 (d), 124.7 (d), 123.8 (d), 122.8 (d), 117.9 (d), 62.3 (t), 39.5 (t), 34.3 (d), 29.2 (d), 26.3 (t), 25.7 (q), 24.1 (q), 24.1 (q), 23.7 (q), 23.7 (q), 17.7 (q), 16.4 (q); LREIMS: m/z (relative abundance) 446 (M$^+$, <0.5), 309 (100), 265 (29), 249 (52), 231 (28), 221 (49), 149 (52), 93 (34), 69 (55), 41 (53).

c) (E)-3,3-Dimethyl-5-(2',2',3'-trimethyl-3'-cyclopenten-1'-yl)-4-penten-2-yl 2-(2',4'-diisopropylbenzoyl)benzoate (4)

2-(2',4'-Diisopropylbenzoyl)benzoic acid (0.3114 g, 1.0 mmol) was dissolved in dry pyridine (2 mL) in a flame-dried round bottom flask. To the solution were added Polysantol® (0.2113 g, 0.95 mmol), 4-dimethylaminopyridine (DMAP) on polystyrene resin (0,168 g, 0.34 mmol) and 1,3-diisopropylcarbodiimide (DIC, 120 μL, 1.4 mmol).

The reaction mixture was stirred at room temperature under an atmosphere of dry nitrogen for 68 hours. The reaction mixture was filtered, and partitioned between 0.5M aqueous hydrochloric acid and ethyl acetate. The organic phase was washed a second time with 0.5M hydrochloric acid, then once with 10% aqueous sodium carbonate solution. The ethyl acetate solution was washed with saturated, aqueous sodium bicarbonate solution and finally with water. The organic phase was dried over anhydrous sodium sulfate, filtered and concentrated under vacuum. The resulting ester was purified by normal phase silica gel chromatography (2% ethyl acetate/cyclohexane) to yield a 1:1 mixture of two stereoisomers in the form of an oil (isolated yield=0.14 g, % yield=27%) which showed the following analytical data:

IR: (neat) 2960, 1720, 1675 cm$^{-1}$, $^1$H NMR (360 MHz, CDCl$_3$) δ ppm: 7.83 (m, 1H), 7.52 (m, 2H), 7.39 (m, 1H), 7.30 (d, 1H, J=1 Hz), 7.12 (dd, 1H, J=2, 8 Hz), 6.94 (dd, 1H, J=2, 8 Hz), 5.39 (2H, m), 5.21 (1H, m), 4.82 (1H, m), 3.83 (1H, m), 2.90 (1H, m), 2.26 (1H, m), 2.17 (1H, m), 2.03 (1H, m), 1.59 (3H, br d, J=1 Hz), 1.30 (6H, d, J=7 Hz), 1.24 (6H, d, J=7 Hz), 0.99, 0.99 (3H, d, J=6 Hz), 0.97, 0.95 (6H, br s), 0.90, 0.87 (3H, s), 0.69, 0.69 (3H, s); $^{13}$C NMR (90 MHz, CDCl$_3$) δ ppm: 198.5 (s), 166.5 (s), 152.8 (s), 150.8 (s), 148.1 (s), 143.0 (s), 136.7 (s), 136.6 (s), 134.3 (s), 131.9 (s), 131.5 (d), 131.0 (d), 129.8 (d), 129.5 (d), 129.5 (d), 129.3 (d), 128.8 (d), 124.8 (d), 122.6 (d), 121.5 (d), 78.3 (d), 78.2 (d), 54.3 (d), 48.1 (s), 48.1 (s), 39.9 (s), 35.5 (t), 34.4 (d), 29.1 (d), 25.4 (q), 24.2 (q), 24.2 (q), 23.7 (q), 23.7 (q), 23.4 (q), 23.2 (q), 20.5 (q), 14.8 (q), 14.7 (q), 12.7 (q); Nanospray MS: m/z (relative abundance) 537.4 ([M+Na]$^+$, 100), 515.2 ([M+H]$^+$, 2).

EXAMPLE 2

Preparation of α-keto Esters

The bis(3,7-dimethyl-6-octenyl)oxalate which was used for the synthesis of some of the α-keto esters described below was prepared as follows.

Oxalyl chloride (10 ml, 116 mmol) was added dropwise to a stirred solution of 36.37 g (233 mmol) of citronellol in 300 ml of pyridine at 0° C. over a period of 30 min. The formation of a white precipitate was observed. The solution was allowed to warm up at room temperature over night and was quenched with water, extracted with diethyl ether (2×), H$_2$SO$_4$ (10%) (2×), NaHCO$_3$ (10%) and saturated NaCl. The organic layer was dried over Na$_2$SO$_4$, concentrated at reduced pressure and filtered over a short plug (SiO$_2$, heptane/diethyl ether). Column chromatography (SiO$_2$, heptane/diethyl ether) gave 18.55 g (43%) of a colorless oil.

IR (neat): 2965s, 2925s, 2873m, 2856m, 1770s, 1745s, 1457m, 1380m, 1347w, 1312m, 1250w, 1170s, 1122w, 1044w, 941m, 886w, 831w, 792w, 756w, 742w. $^1$H NMR (360 MHz, CDCl$_3$): 5.13–5.04 (m, 1H); 4.40–4.23 (m, 2H); 2.08–1.87 (m, 2H); 1.85–1.71 (m, 1H); 1.70–1.50 (m, 2H); 1.68 (s, 3H); 1.60 (s, 3H); 1.43–1.29 (m, 1H); 1.29–1.13 (m, 1H); 0.94 (d, J=6.3, 3H). $^{13}$C NMR (90.6 MHz, CDCl$_3$): 158.04 (s); 131.45 (s); 124.42 (d); 65.59 (t); 36.91 (t); 35.08 (t); 29.42 (d); 25.70 (q); 25.36 (t); 19.36 (q); 17.65 (q). MS (EI): 336 (M$^+$, 0.1); 228 (0.1); 183 (0.1); 165 (0.1); 138 (18); 123 (30); 109 (16);95 (38); 81 (51); 69 (100); 55 (30); 41 (46); 29 (5).

a) 3,7-Dimethyl-6-octenyl 3-Methyl-2-oxopentanoate (5)

A stirred solution of 4.85 g (38 mmol) of 3-methyl-2-oxo pentanoic acid and 11.66 g (74 mmol) of citronellol in 130 ml of toluene was heated for 72 h under reflux with azeotropic removal of water. After cooling to room temperature diethyl ether was added, and the reaction mixture was extracted with 10% Na$_2$CO$_3$ (2×), saturated NaCl, dried (Na$_2$SO$_4$) and concentrated in vacuo. Column chromatography (SiO$_2$, toluene/EtOAc) afforded 10 g of crude product, which was fractionally distilled to give 3.65 g (36%) of a colorless oil.

B.p. 94° C./2×10$^1$ Pa. UV/Vis (hexane): 394 (sh, 4), 382 (sh, 10), 374 (sh, 10), 365 (sh, 10), 350 (sh, 20), 336 (20), 268 (sh, 30), 241 (sh, 180).

IR (neat): 2966s, 2929s, 2877m, 1749m, 1728s, 1460m, 1380m, 1267m, 1254m, 1165m, 1115w, 1087w, 1051m, 1001w, 961w, 829w. $^1$H NMR (360 MHz, CDCl$_3$):

5.12–5.04 (m, 1H); 4.36–4.24 (m, 2H); 3.18–3.06 (m, 1H); 2.08–1.88 (m, 2H); 1.86–1.67 (m, 2H); 1.68 (s, 3H); 1.65–1.10 (m, 5H; 1.60 (s, 3H); 1.28 (d, J=6.8, 3H); 0.94 (d, J=6.4, 3H); 0.92 (t, J=7.6, 3H). $^{13}$C NMR (90.6 MHz, CDCl$_3$): 198.22 (s); 162.21 (s); 131.51 (s); 124.40 (d); 64.74 (t); 43.64 (d); 36.92 (t); 35.23 (t); 29.43 (d); 25.71 (q); 25.36 (t); 24.93 (t); 19.35 (q); 17.66 (q); 14.55 (q); 11.35 (q). MS (EI): 268 (M$^+$, 1); 250 (1); 240 (1); 207 (1); 183 (2); 155 (2); 138 (10); 123 (14); 109 (7); 95 (18); 85 (32); 81 (26); 69 (51); 57 (100); 41 (53); 29 (18).

b) 3,7-Dimethyl-6-octenyl 2-Oxopentanoate (6)

The synthesis was carried out as described above under a), using 4.33 g (37 mmol) of 2-oxo pentanoic acid and 11.65 g (75 mmol) of citronellol. Column chromatography (SiO$_2$, toluene/EtOAc and SiO$_2$, heptane/diethyl ether) afforded 3.79 g of crude product, which was distilled (Kugelrohr) to give 2.52 g (27%) of a colorless oil.

UV/Vis (hexane): 398 (sh, 1), 376 (sh, 10), 357 (sh, 10), 342 (sh, 20), 331 (20), 281 (sh, 20), 268 (sh, 30), 241 (sh, 280). IR (neat): 2965s, 2931s, 2877m, 1750m, 1728s, 1457m, 1380m, 1287w, 1261m, 1178w, 1146w, 1118m, 1055m, 1037w, 943w, 832w. $^1$H NMR (360 MHz, CDCl$_3$): 5.13–5.03 (m, 1H); 4.36–4.21 (m, 2H); 2.80 (t, J=7.1, 2H); 2.10–1.89 (m, 2H); 1.83–1.70 (m, 1H); 1.68 (s, 3H); 1.67 (q, J=7.3, 2H); 1.63–1.47 (m, 2H); 1.60 (s, 3H); 1.45–1.29 (m, 1H); 1.28–1.12 (m, 1H); 0.96 (t, J=6.9, 3H); 0.94 (d, J=6.3, 3H). $^{13}$C NMR (90.6 MHz, CDCl$_3$): 194.63 (s); 161.44 (s); 131.52 (s); 124.40 (d); 64.88 (t); 41.21 (t); 36.91 (t); 35.19 (t); 29.43 (d); 25.71 (q); 25.35 (t); 19.37 (q); 17.67 (q); 16.54 (t); 13.52 (q). MS (EI): 254 (M$^+$, 1); 236 (2); 226 (1); 193 (1); 183 (6); 165 (1); 155 (7); 138 (15); 137 (10); 123 (26); 118 (3); 109 (17); 95 (41); 83 (15); 82 (32); 81 (54); 71 (87); 69 (100); 67 (23); 55 (34); 43 (66); 41 (72); 27 (14).

c) 3,7-Dimethyl-6-octenyl Oxo(phenyl)acetate (7)

A Grignard reagent prepared from 3.14 g of 1-bromobenzene (20 mmol) and 0.55 g of magnesium (22 mmol) in THF was added dropwise to a stirred solution of 8.0 g (22 mmol) of bis(3,7-dimethyl-6-octenyl)oxalate in 50 ml of THF at −78° C. The mixture was slowly warmed to −10° C., quenched with 25–30 ml of a saturated solution of NH$_4$Cl and left stirring for 30 min. The reaction mixture was extracted with diethyl ether and water (3×) and the organic phase dried over Na$_2$SO$_4$. MPLC on a Lobar column (SiO$_2$ Merck, heptane/diethyl ether) afforded 3.5 g (61%) of the pure product as a bright yellow oil.

UV/Vis (hexane): 370 (sh, 30), 352 (40), 340 (sh, 40), 294 (sh, 1020), 252 (10350), 248 (10360). IR (neat): 3065w, 2962s, 2926s, 2872m, 2855m, 1738s, 1693s, 1597m, 1581m, 1451m, 1379m, 1322m, 1313m, 1300m, 1246w, 1198s, 1175s, 1122w, 1042w, 1030w, 1003m, 998m, 941w, 831w. $^1$H NMR (360 MHz, CDCl$_3$): 8.04–7.97 (m, 2H); 7.69.7.62 (m, 1H); 7.55–7.45 (m, 2H); 5.12–5.03 (m, 1H); 4.50–4.36 (m, 2H); 2.15–1.90 (m, 2H); 1.90–1.75 (m, 1H); 1.75–1.50 (m, 2H); 1.66 (s, 3H); 1.59 (s, 3H); 1.45–1.32 (m, 1H); 1.32–1.15 (m, 1H); 0.96 (d, J=6.3, 3H). $^{13}$C NMR (90.6 MHz, CDCl$_3$): 186.50 (s); 164.02 (s); 134.87 (d); 132.56 (s); 131.51 (s); 130.02 (d); 128.90 (d); 124.40 (d); 64.85 (t); 36.93 (t); 35.30 (t); 29.44 (d); 25.69 (q); 25.38 (t); 19.38 (q); 17.66 (q). MS (EI): 288 (M$^+$, 1); 270 (4); 260 (1); 227 (1); 215 (1); 187 (1); 174 (1); 165 (1); 155 (4); 152 (3); 138 (9); 137 (10); 134 (2); 123 (11); 109 (8); 106 (10); 105 (100); 96 (3); 95 (20); 83 (3); 82 (12); 81 (24); 80 (2); 78 (3); 77 (36); 70 (3); 69 (26); 68 (5); 67 (10); 57 (3); 56 (3); 55 (11); 53 (3); 51 (10); 43 (4); 42 (3); 41 (28); 39 (5); 29 (4); 27 (4).

d) 3,7-Dimethyl-6-octenyl(4-acetylphenyl) Oxoacetate (8)

In the first step, 2-(4-bromomethyl)-2-methyl-1,3-dioxolane was prepared as follows. 10.0 g (50 mmol) of 4-bromo acetophenone, 7.0 g (112 mmol) of ethylene glycol and a few crystals of p-toluene sulphonic acid were dissolved in 100 ml of toluene and heated overnight under reflux with azeotropic removal of water. After cooling to room temperature the reaction mixture was concentrated in vacuo. Column chromatography (SiO$_2$, heptane/diethyl ether) afforded 11.4 g (93%) of a colorless oil which easily crystallized.

UV/Vis (hexane): 287 (sh, 400), 274 (sh, 1300), 270 (sh, 1800), 259 (sh, 6700), 252 (7800), 227 (sh, 61800), 220 (75600), 217 (sh, 75000). IR (neat): 3084w, 3060w, 2990m, 2957s, 2928s, 2890s, 2856m, 2670w, 1911w, 1691m, 1657w, 1591m, 1575w, 1482m, 1470w, 1443m, 1393m, 1373m, 1249m, 1222w, 1196s, 1144m, 1118m, 1092m, 1079m, 1040s, 1010s, 947m, 873s, 826s. $^1$H NMR (360 MHz, CDCl$_3$): 7.49–7.42 (m, 2H); 7.39–7.32 (m, 2H); 4.08–3.96 (m, 2H); 3.80–3.69 (m, 2H); 1.62 (s, 3H). $^{13}$C NMR (90.6 MHz, CDCl$_3$): 142.49 (s); 131.30 (d); 127.17 (d); 121.86 (s); 108.43 (s); 64.47 (t); 27.52 (q). MS (EI): 244, 242 (M$^+$, 1, 1); 230 (14); 229 (97); 227 (100); 213 (5); 211 (5); 186 (4); 185, 183 (51, 53); 171 (2); 169 (2); 157, 155 (14, 14); 148 (4); 133 (5); 105 (2); 104 (8); 103 (9); 102 (8); 101 (2); 89 (3); 87 (26); 78 (2); 77 (12); 76 (16); 75 (14); 74 (7); 73 (2); 63 (4); 62 (2); 51 (7); 50 (13); 43 (41); 39 (3); 29 (7).

The thus obtained compound was then used as starting product for the synthesis of 3,7-Dimethyl-6-octenyl [4-(2-methyl-1,3-dioxolan-2-yl)phenyl]-oxoacetate. The synthesis was carried out as described above under c), using 4.66 g (20 mmol) of the above-prepared dioxolane, 0.54 g (22 mmol) of magnesium and 8.0 g (22 mmol) of bis(3,7-dimethyl-6-octenyl)oxalate. Column chromatography (SiO$_2$, heptane/diethyl ether) afforded 4.35 g (58%) of the product as a slightly yellow oil.

UV/Vis (hexane): 370 (sh, 40), 353 (60), 340 (sh, 60), 296 (sh, 1300), 258 (13890). IR (neat): 2963s, 2926s, 1736s, 1690s, 1607s, 1573m, 1505w, 1455m, 1407m, 1374m, 1347w, 1314m, 1294w, 1250m, 1199s, 1175s, 1146w, 1122w, 1100w, 1078m, 1039m, 1018w, 989m, 948w, 890w, 876m, 861m, 833w. $^1$H NMR (360 MHz, CDCl$_3$): 7.98 (d, J=8.3, 2H); 7.62 (d, J=8.7, 2H); 5.12–5.04 (m, 1H); 4.50–4.36 (m, 2H); 4.13–4.00 (m, 2H); 3.82–3.70 (m, 2H); 2.10–1.90 (m, 2H); 1.90–1.75 (m, 1H); 1.72–1.54 (m, 2H); 1.67 (s, 3H); 1.65 (s, 3H); 160 (s, 3H); 1.45–1.32 (m, 1H); 1.30–1.16 (m, 1H); 0.96 (d, J=6.3, 3H). $^{13}$C NMR (90.6 MHz, CDCl$_3$): 186.04 (s); 163.97 (s); 150.64 (s); 132.12 (s); 131.53 (s); 130.15 (d); 125.97 (d); 124.39 (d); 108.39 (s); 64.89 (t); 64.65 (2×) (t); 36.93 (t); 35.30 (t); 29.44 (d); 27.38 (q); 25.70 (q); 25.37 (t); 19.38 (q); 17.66 (q). MS (EI): 374 (M$^+$, 7); 359 (8); 356 (3); 289 (1); 220 (2); 205 (1); 192 (32); 191 (100); 176 (2); 160 (2); 155 (2); 148 (24); 138 (16); 133 (6); 123 (14); 119 (76); 109 (9); 104 (15); 95 (22); 91 (8); 87 (18); 81 (30); 69 (26); 55 (10); 43 (12); 41 (21); 29 (3).

3,7-Dimethyl-6-octenyl (4-Acetylphenyl)oxoacetate (8) 5 ml of H$_2$SO$_4$ (50%) were added to a soln. of 4.2 g (13 mmol) of the product obtained in the above step in 30 ml of THF. The reaction mixture was heated at 40° C. for 5 h, then extracted with diethyl ether (2×), and saturated solutions of NaHCO$_3$ (2×) and NaCl (2×). The organic layer was dried over Na$_2$SO$_4$ and concentrated. Column chromatography (SiO$_2$, heptane/diethyl ether) yielded 2.0 g (47%) of a yellow oil.

UV/Vis (hexane): 384 (sh, 60), 367 (sh, 100), 343 (sh, 150), 310 (sh, 1230), 301 (sh, 1660), 266 (17910), 260 (18440). IR (neat): 3051w, 2964s, 2926s, 2872m, 2856m, 1736s, 1693s, 1607w, 1570m, 1500m, 1457m, 1434m, 1407m, 1379m, 1359m, 1318m, 1307m, 1260s, 1199s, 1176s, 1117w, 1075m, 992s, 959m, 861m, 832m. $^1$H NMR (360 MHz, CDCl$_3$): 8.17–8.02 (m, 4H); 5.12–5.04 (m, 1H); 4.53–4.37 (m, 2H); 2.66 (s, 3H); 2.14–1.90 (m, 2H); 1.90–1.75 (m, 1H); 1.73–1.53 (m, 2H); 167 (s, 3H); 1.60 (s, 3H); 1.46–1.32 (m, 1H); 1.32–1.12 (m, 1H); 0.96 (d, J=6.3, 3H). $^{13}$C NMR (90.6 MHz, CDCl$_3$): 197.19 (s); 185.55 (s); 163.25 (s); 141.33 (s); 135.67 (s); 131.57 (s); 130.28 (d); 128.56 (d); 124.34 (d); 65.19 (t); 36.91 (t); 35.26 (t); 29.43 (d); 26.94 (q); 25.70 (q); 25.35 (t); 19.37 (q); 17.67 (q). MS (EI): 330 (M$^+$, 4); 312 (1); 302 (1); 281 (1); 269 (1); 194 (4); 193 (2); 183 (5); 176 (2); 165 (1); 161 (1); 155 (2); 149 (5); 148 (43); 147 (100); 138 (4); 137 (11); 133 (1); 132 (2); 123 (10); 120 (4); 119 (11); 110 (2); 109 (10); 105 (2); 104 (12); 96 (4); 95 (21); 91 (15); 83 (5); 82 (13); 81 (29); 77 (6); 76 (8); 69 (38); (5); 67 (11); 65 (3); 57 (3); 56 (3); 55 (12); 53 (3); 50 (3); 43 (15); 41 (30); 39 (5); 29 (4); 27 (3).

e) 3,7-Dimethyl-6-octenyl 3-Methyl-2-oxopentadecanoate (9)

The compound was prepared as described above under c), using 5.0 g (18 mmol) of 2-bromotetradecane, 0.58 g (24 mmol) of magnesium and 7.32 g (20 mmol) of bis(3,7-dimethyl-6-octenyl)oxalate. Column chromatography (SiO$_2$, heptane/diethyl ether) afforded 2.52 g (34%) of a colorless oil.

UV/Vis (hexane): 394 (sh, 4), 383 (sh, 10), 373 (sh, 10), 365 (sh, 20), 349 (sh, 20), 336 (20), 284 (sh, 10), 269 (sh, 20), 241 (sh, 140). IR (neat): 3440w, 2958s, 2924s, 2854s, 2730w, 1749s, 1725s, 1460m, 1378m, 1350w, 1266m, 1173w, 1146w, 1112w, 1053m, 1032m, 943w, 887w, 830w. $^1$H NMR (360 MHz, CDCl$_3$): 5.13–5.04 (m, 1H); 4.36–4.23 (m, 2H); 3.23–3.10 (m, 1H); 2.10–1.87 (m, 2H); 1.87–1.64 (m, 1H); 1.68 (s, 3H); 1.64–1.47 (m, 2H); 1.60 (s, 3H); 1.46–1.16 (m, 24H); 1.13 (d, J=6.7, 3H); 0.94 (d, J=6.3, 3H); 0.88 (t, J=6.9, 3H). $^{13}$C NMR (90.6 MHz, CDCl$_3$): 198.33 (s); 162.20 (s); 131.50 (s); 124.40 (d); 64.75 (t); 42.21 (d); 36.93 (t); 35.23 (t); 31.92 (t); 29.68 (t); 29.66 (2×) (t); 29.59 (2×) (t); 29.45 (2×) (t); 29.37 (t); 27.01 (t); 25.71 (q); 25.37 (t); 22.70 (t); 19.35 (q); 17.66 (q); 15.01 (q); 14.12 (q). MS (EI): 408 (M$^+$, 1); 390 (1); 380 (1); 347 (1); 294 (1); 272 (1); 255 (4); 205 (1); 197 (3); 184 (2); 183 (12); 165 (1); 155 (8); 141 (4); 139 (9); 138 (76); 137 (21); 127 (7); 123 (46); 113 (9); 109 (19); 99 (15); 96 (15); 95 (57); 94 (8); 85 (47); 83 (25); 82 (52); 81 (89); 80 (14); 71 (65); 70 (10); 69 (100); 68 (10); 67 (18); 57 (94);56 (17); 55 (51); 43 (61); 41 (69); 39 (7); 29 (15); 27 (6).

f) 3,7-Dimethyl-6-octenyl 2-Oxohexadecanoate (10)

The compound was prepared as described above under c), using 5.54 g (20 mmol) of 1-bromotetradecane, 0.54 g (22.5 mmol) of magnesium and 8.0 g (22 mmol) of bis(3,7-dimethyl-6-octenyl)oxalate. Column chromatography (SiO$_2$, heptane/diethyl ether) afforded 3.21 g (39%) of a colorless oil.

UV/Vis (hexane): 376 (sh, 10), 359 (sh, 20), 343 (sh, 20), 279 (260), 272 (sh, 250), 242 (530). IR (neat): 2958m, 2924s, 2854s, 1728s, 1465m, 1458m, 1400w, 1378m, 1271m, 1128w, 1088w, 1062m, 945w, 831 w. $^1$H NMR (360 MHz, CDCl$_3$): 5.12–5.03 (m, 1H); 4.35–4.21 (m, 2H); 2.81 (t, J=7.3, 2H); 2.09–1.88 (m, 2H); 1.87–1.69 (m, 1H); 1.68 (s, 3H); 1.69–1.47 (m, 2H); 1.60 (s, 3H); 1.45–1.14 (m, 26H); 0.94 (d, J=6.3, 3H); 0.88 (t, J=6.9, 3H). $^{13}$C NMR (90.6 MHz, CDCl$_3$): 194.77 (s); 161.48 (s); 131.49 (s); 124.41 (d); 64.86 (t); 39.38 (t); 36.93 (t); 35.20 (t); 31.96 (t); 29.68 (3×) (t); 29.61 (t); 29.45 (2×) (t); 29.39 (t); 29.33 (t); 29.01 (t); 25.71 (q); 25.37 (t); 23.05 (t); 22.71 (t); 19.38 (q); 17.66 (q); 14.12 (q). MS (EI): 390 (1), 225 (11), 183 (14), 165 (1), 155 (8), 139 (7), 138 (55), 137 (28), 124 (6), 123 (52), 121 (5), 111 (4), 110 (7), 109 (27), 97 (9), 96 (16), 95 (70), 94 (8), 85 (16), 83 (28), 82 (50), 81 (97), 80 (10), 71 (26), 70(11), 69 (100), 68 (11), 67 (21), 57 (54), 56 (12), 55 (47), 43 (48), 42 (10), 41 (55), 39 (7), 29 (12).

g) 3,7-Dimethyl-6-octenyl(cyclohexyl)Oxoacetate (11)

The compound was prepared as described above under c), using 3.24 g (20 mmol) of freshly distilled 1-bromocyclohexane, 0.55 g (22 mmol) of magnesium and 8.0 g (22 mmol) of bis(3,7-dimethyl-6-octenyl)oxalate. MPLC on a Lobar column (SiO$_2$ Merck, heptane/diethyl ether) finally afforded 1.69 g (29%) of the pure product as a colorless oil.

UV/Vis (hexane): 394 (sh, 4), 375 (sh, 11), 366 (sh, 14), 350 (sh, 18), 338 (19). IR (neat): 2932s, 2856m, 1747m, 1727s, 1451m, 1379m, 1311w, 1276m, 1230m, 1183w, 1173w, 1140m, 1118w, 1082m, 1067m, 1050w, 1029w, 997m, 942w, 895w, 837w. $^1$H NMR (360 MHz, CDCl$_3$): 5.12–5.04 (m, 1H); 4.36–4.22 (m, 2H); 3.07–2.95 (m, 1H); 2.09–1.85 (m, 4H); 1.85–1.64 (m, 3H); 1.68 (s, 3H); 1.64–1.47 (m, 2H); 1.60 (s, 3H); 1.43–1.13 (m, 8H); 0.93 (d, J=6.3, 3H). $^{13}$C NMR (90.6 MHz, CDCl$_3$): 197.65 (s); 162.17 (s); 131.51 (s); 124.39 (d); 64.71 (t); 46.34 (d); 36.91 (t); 35.21 (t); 29.44(d); 27.46 (t); 25.72 (t); 25.36 (t); 25.30 (t); 19.35 (q); 17.66 (q). MS (EI): 294 (M$^+$, 1); 276 (1); 266 (1); 233 (1); 193 (1); 183 (4); 165 (1); 155 (2); 139 (2); 138 (13); 137 (4); 123 (14); 112 (2); 111 (16); 110 (3); 109 (6); 96 (4); 95 (16); 94 (2); 84 (7); 83 (100); 82 (15); 81 (22); 80 (3); 70 (2); 69 (29); 68 (4); 67 (11); 56 (4); 55 (42); 54 (3); 53 (5); 43 (4); 42 (4); 41 (38); 39 (8); 29 (6); 27 (4).

EXAMPLE 3

Release of Geraniol from Solutions of Geranyl 2-Benzoyl benzoate

Geranyl 2-benzoyl benzoate was dissolved in a concentration of 3.68g/l in the solvents indicated in Table 1. The samples were then irradiated using a Fadeometer and under the conditions indicated in Table 1, and the amount of released geraniol was measured. The values indicated are the average of duplicate samples.

TABLE 1

Release of geraniol from geranyl 2-benzoyl benzoate in solution upon irradiation with a Fadeometer

| Run | Solvent | Length of photolysis (KJ/m$^2$) | % of geraniol released* |
|---|---|---|---|
| 1 | Isopropanol/benzene 1:1 | 33.7 | 24.4 |
| 2 | Isopropanol/benzene 1:1 | 3.4 | 30.4 |
| 3 | Isopropanol/benzene 1:1 | 0** | 0 |
| 4 | Dodecanol/benzene 1:1 | 33.7 | 26.8 |
| 5 | Isopropanol/acetonitrile | 3.4 | 22.6 |
| 6 | Isopropanol/acetonitrile | 0** | 0 |

*calculated as weight % of theoretically possible geraniol release
**indicates a control run in which the flask was wrapped with aluminum foil before irradiation The following Table 2 indicates the amount of geraniol released from the same ester, but upon exposure to sunlight (New Jersey, USA, typical sunny day of June).

TABLE 2

Release of geraniol from geranyl 2-benzoyl benzoate in solution upon exposure to sunlight

| Run | Solvent | Hours of sun exposure | % of geraniol released* |
|---|---|---|---|
| 1 | Isopropanol/benzene 1:1 | 5 | 71.3 |
| 2 | Isopropanol/benzene 1:1 | 0** | 0 |

*calculated as weight % of theoretically possible geraniol release
**indicates a control run in which the flask was wrapped with aluminum foil before irradiation The above results show that it is possible to release geraniol in solution upon exposure to a Fadeometer or to sunlight, while no release occurs when the sample is not exposed to radiation.

EXAMPLE 4
Release of Geraniol from Geranyl 2-(2'-isopropylbenzoyl) Benzoate (Solution and Film)

Geranyl 2-(2-isopropylbenzoyl)benzoate was dissolved in a concentration of 4.05g/l in benzene and subsequently irradiated, or was deposited as a thin film, by the method described above, on the walls of the flask before irradiation. After irradiation, the amount of released geraniol was measured. The results are shown in Table 3. The values indicated are the average of duplicate samples.

TABLE 3

Release of geraniol from geranyl 2-(2'-isopropylbenzoyl)benzoate in solution and as a film upon irradiation with a Fadeometer

| Run | Solvent/film | Length of photolysis ($KJ/m^2$) | % of geraniol released* |
|---|---|---|---|
| 1 | Benzene | 3.4 | 11.2 |
| 2 | Benzene | 0** | 0 |
| 3 | Film (33.5 mg) | 3.4 | 9.5 |
| 4 | Film (32.5 mg) | 0** | 0 |

*calculated as weight % of theoretically possible geraniol release
**indicates a control run in which the flask was wrapped with aluminum foil before irradiation Table 4 indicates the results of analogous experiments in which the solutions and films of geranyl 2-(2'-isopropylbenzoyl)benzoate were exposed to sunlight (New Jersey, USA, typical sunny day of June). The values indicated are the average of duplicate samples.

TABLE 4

Release of geraniol from geranyl 2-(2'-isopropylbenzoyl)benzoate (solution and film) upon exposure to sunlight

| Run | Solvent/film | Hours of sun exposure | % of geraniol released* |
|---|---|---|---|
| 1 | Isopropanol/benzene 1:1 | 5 | 71.3 |
| 2 | Isopropanol/benzene 1:1 | 0** | 0 |
| 3 | Film (14.2 mg) | 5 | 27.0 |
| 4 | Film (14.2 mg) | 0** | 0 |

*calculated as weight % of theoretically possible geraniol release
**indicates a control run in which the flask was wrapped with aluminum foil before irradiation The above results show that the introduction of an isopropyl substituent into the geranyl ester allows the release of geraniol from solution and from a solid film, upon exposure to a Fadeometer radiation and to natural sunlight.

EXAMPLE 5
Release of Geraniol from Geranyl 2-(2',4'-diisopropylbenzoyl)benzoate (Solution and Film)

Geranyl 2-(2',4'-diisopropylbenzoyl)benzoate was dissolved in benzene in a concentration of 4.48 g/l in benzene and subsequently irradiated, using a Fadeometer. The samples were irradiated with 31.1 $KJ/m^2$, and 50 weight % of the theoretical value of geraniol was released.

Similar experiments were conducted in which benzene solutions with the same content in geranyl 2-(2',4'-diisopropylbenzoyl)benzoate and films which were obtained as described above, were exposed to daylight outdoors (New Jersey, USA, cloudy day in August). Table 5 shows the results of the experiments. The values indicated are the average of duplicate samples.

TABLE 5

Release of geraniol from geranyl 2-(2',4'-diisopropylbenzoyl)benzoate in solution and as film, upon exposure to sunlight

| Run | Solvent/film | Hours of sun exposure | % of geraniol released* |
|---|---|---|---|
| 1 | Benzene | 6 | 13 |
| 2 | Film | 6 | 18 |

*calculated as weight % of theoretically possible geraniol release

EXAMPLE 6
Release of Geraniol from Geranyl 2-(2',4'-Diisopropylbenzoyl)benzoate in an All-purpose Cleaner An all-purpose cleaner of the standard type containing 0.3% of geranyl 2-(2',4'-diisopropylbenzoyl)benzoate was prepared. The all-purpose cleaner solution thus obtained was added to borosilicate flasks which were then irradiated for 13 hours with a 366 nm UV lamp. The resulting solutions were then compared to identical all-purpose cleaner formulations which had not been irradiated, on a triangular blind test by a panel composed of 15 non-experts. The odd sample was the one containing the irradiated all-purpose cleaner solution. The evaluation was carried out by sniffing on the flask.

From the 15 test persons, 12 correctly distinguished the irradiated sample from the non-irradiated samples. They found that the odor note of the irradiated sample was floral, geraniol, citrus or citronellal, whereas the non-irradiated sample was found to be neutral, odorless or slightly oily.

The release of geraniol from the 2-benzoyl benzoate used in the present embodiment and from the other benzoates synthesized occurrred in all types of all-purpose cleaners and is therefore not restricted to one type of these.

EXAMPLE 7
Release of Polysantol® from (E)-3,3-Dimethyl-5-(2',2',3'-trimethyl-3'-cyclopenten-1-yl)-4-penten-2-yl 2-(2',4'-Diisopropylbenzoyl)benzoate The above-identified compound was dissolved in toluene in a concentration of 2.35 g/l and irradiated for 6 hours with a UV lamp. The amount of released Polysantol was measured by GC, and it was found that 35% of the theoretical amount of Polysantol had been released.

EXAMPLE 8
Release of Cironellal from Various Citronellyl α-keto Esters 0.01 M solutions (5 ml) of the α-keto esters prepared as described in example 2, in toluene or ethanol, were prepared and irradiated with a xenon or a UV lamp in 10 ml volumetric flasks. Samples in the neat state were also irradiated under the same conditions. Before irradiation in solution, 1 ml of a 0.01 M solution of decanol was added which served as internal standard for GC analysis. The results are found in the Table 6 below. Table 6 indicates the amount of released citronellal in mol %, the amounts or remaining starting material are indicated in brackets. It was also observed that olefins were released, from compounds (9) and (10) of example 2, together with release of citronellal.

TABLE 6

Results of the photoirradiations of different α-keto esters in solution and in their neat state

| Compound N° | Lamp | Yield of citronellal and olefin released (remaining starting material[a]) in mol %) | | | | | |
|---|---|---|---|---|---|---|---|
| | | Toluene 3 h | | Ethanol 3 h | | Neat 3.5 h | |
| 5 | Xenon | 55 | (<5) | 45 | (n.d.) | 5 | (39) |
|   | UV    | 19 | (60) |    |        |   |      |
| 6 | Xenon | 38 | (<5) | 17 | (n.d.) | 1 | (47) |
|   | UV    | 13 | (75) |    |        |   |      |
| 7 | Xenon | 33 | (10) | 17 | (n.d.) | <1 | (1) |
|   | UV    | 13 | (65) |    |        |   |      |
| 8 | Xenon | 9  | (20) | 3  | (n.d.) | <1 | (2) |
|   | UV    | 4  | (55) |    |        |   |      |
| 9 | Xenon | 11 | (30) | 6  | (n.d.) | 2/11[c] | (31) |
|   | UV    | 2/6[c] | (85) | | | | |
| 10 | Xenon | 8 | (50) | 2 | (n.d.) | 1/10[b] | (34) |
|    | UV    | 0/2[b] | (85) | | | | |
| 11 | Xenon | ≈45 | (<5) | 43 | (n.d.) | 3 | (33) |
|    | UV    | 25 | (65) | | | | |

[a] values in brackets indicate amounts of remaining starting material rounded to ±5%
[b] first number indicates mol % of citronellal, second number indicates mol-% of tridecene liberated by hydrogen abstraction from the alkyl chain
[c] first number indicates mol % of citronellol, second number indicates mol-% of dodecene liberated by hydrogen abstraction of the alkyl chain
n.d.: not determined

EXAMPLE 9
Release of Citronellal from Various Citronellyl α-keto Esters in After-shave Lotions Compounds (5) and (6) of example 2 were each dissolved in an amount of 0.29 g in 19.54 g of a standard after-shave lotion base, under addition of a standard solubilizer (Cremophor RH40, BASF AG). For each of the compounds, three samples of 6 ml (one of which was wrapped in aluminium foil to serve as reference) were irradiated in 10 ml volumetric flasks for 3h with a xenon lamp. The irradiated samples were analyzed by HPLC using citronellal and the corresponding starting materials as external standards. The reference experiment (aluminium foil wrapped) showed no release of citronellal. The results obtained with the other samples are summarized in Table 7.

TABLE 7

Results of the photoirradiations of α-keto esters in after-shave lotion

| Compound N° | mol-% of citronellal liberated | mol-% of remaining* starting material |
|---|---|---|
| 5 | 12 | 36 |
| 6 | 2  | 53 |

*average of 2 samples

EXAMPLE 10
Release of Citronellal from Various Citronellyl α-keto Esters in a Window Cleaner and in an All-purpose Cleaner 10 mg of the respective α-keto ester as specified in Table 10 below were weighed into 10 ml volumetric flasks. A solubilizer was added (Cremophor RH40, BASF AG for window cleaner, Triton X100 (Rohm & Haas) for all-purpose cleaner), before adding 6 ml of the respective base, i.e. a standard type window cleaner, or a Fabuloso® (registered trademark of Colgate-Palmolive, USA) type all-purpose cleaner, and agitating until the solution became clear. For each irradiation series four samples were prepared for each compound, one of which, wrapped in aluminium foil, served as reference. All the samples were irradiated for 3, 6, or 15 h with either the Xenon or the UV lamp. In all cases the formation of citronellal could be smelled after the photolysis. In order to quantify the amount of aldehyde (and of the remaining starting material) in the application base, the irradiated samples were subjected to GC analysis (extraction and on-column injection).

For analysis, 1 g of NaCl was added and the samples were extracted with 5 ml of a 0.32 mM (5 mg/l) solution of undecane (used as internal standard) in iso-octane. The aqueous layer was re-extracted with 2 ml of the iso-octane solution and the two organic phases were combined and injected directly onto a GC column. The results obtained for the different bases are summarized in Table 8.

TABLE 8

Results of the photoirradiations of different α-keto esters in different household application bases

| Compound N° | Tested Application | Lamp | Irradiation Time | Yield of* Citronellal in mol-% | Remaining* Starting Material in mol-% | Smell |
|---|---|---|---|---|---|---|
| 5 | Window Cleaner (solution) | Xenon | 3 h | 7.5 | 17 | |
|   | Window Cleaner (solution) | UV | 3 h | 2.2 | 91 | citronellal |
|   |   |   | 6 h | 3.4 | 69 | citronellal |
|   |   |   | 15 h | 5.7 | 39 | |
|   | All-purpose cleaner (solution) | UV | 3 h | 2.1 | 73 | citronellal |
|   |   |   | 15 h | 8.3 | 42 | strong citronellal |
| 7 | Window Cleaner (solution) | UV | 3 h | 0.8 | 44 | weak citronellal |
| 11 | Window Cleaner (solution) | Xenon | 3 h | 3.0 | 13 | citronellal |
|    | Window Cleaner (solution) | UV | 3 h | 3.0 | 81 | citronellal |
|    |   |   | 6 h | 2.7 | 71 | strong citronellal |
|    |   |   | 15 h | 6.0 | 33 | |

TABLE 8-continued

Results of the photoirradiations of different α-keto esters in different household application bases

| Compound N° | Tested Application | Lamp | Irradiation Time | Yield of* Citronellal in mol-% | Remaining* Starting Material in mol-% | Smell |
|---|---|---|---|---|---|---|
| | All-purpose cleaner (solution) | UV | 3 h<br>15 h | 0.8<br>10.8 | 82<br>37 | weak citronellal<br>strong citronellal |

*average of 3 samples

What is claimed is:

1. A perfuming composition containing a compound of formula

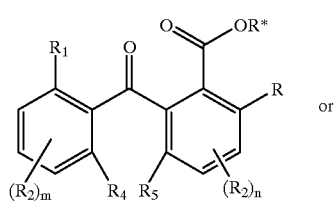

(I)

or

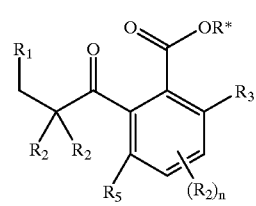

(II)

in which $R_1$ represents hydrogen or a group of formula $$—CH—X$$
$$\phantom{—C}|\phantom{—X}$$
$$\phantom{—CH}Y$$

in which X and Y can be identical or different and represent hydrogen, a linear or branched alkyl or alkoxy group from $C_1$ to $C_{12}$, a phenyl group, an olefinic group from $C_2$ to $C_{12}$, an alcohol group, a $CO_2M$ group, a $—NR_6R_7$ group or a group of formula

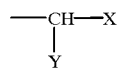

$R_2$ can be identical to $R_1$ or different from it and represents hydrogen, a linear or branched alkyl or alkoxy group from $C_1$ to $C_{12}$, a phenyl group, an olefinic group from $C_2$ to $C_{12}$, an alcohol group, a $CO_2M$ group, a $—NR_6R_7$ group or a group of formula

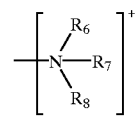

or a polyalcohol or polyether group;

$R_3$ represents hydrogen, an alkyl or alkoxy group from $C_1$ to $C_4$, linear or branched, a OH group or a $NH_2$ group;

$R_4$ and $R_5$, taken separately, have the meaning given above for $R_1$ and can be identical to or different from $R_1$ or from each other; or $R_4$ and $R_5$, taken together, form a bridging group between the two aromatic rings, which bridging group can be a methylene or a keto group;

m is an integer from 0 to 3 and n is an integer from 0 to 2; $R_6$ and $R_7$, taken separately, each represents hydrogen, an alkyl group from $C_1$ to $C_4$, an alcohol group having an alkyl chain from $C_1$ to $C_{12}$, or a phenyl group, or, $R_6$ and $R_7$, taken together with the nitrogen atom form a 5-membered or 6-membered ring optionally containing another hetero atom;

$R_8$ represents hydrogen, an alkyl group from $C_1$ to $C_4$, an alcohol group having an alkyl chain from $C_1$ to $C_{12}$ or a phenyl group;

M represents hydrogen or an alkali metal;

R* is the organic part derived from a primary or secondary fragrant alcohol R*OH, wherein the fragrant alcohol is released upon exposure of the composition to light to provide a fragrance; and perfuming ingredients, solvents, and adjuvants suitable for use in a perfuming composition.

2. The perfuming composition according to claim 1, wherein the compound is of the formula

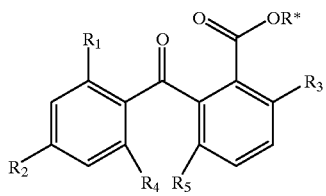

(I')

in which $R_1$ is a branched alkyl group from $C_3$ to $C_4$ containing a secondary hydrocarbon group;

$R_2$ is a branched alkyl group from $C_3$ to $C_4$ and is identical to $R_1$;

R₃ is a hydrogen or a linear or branched alkyl group from C₁ to C₄;

R₄ is a hydrogen or a linear or branched alkyl group from C₁ to C₄;

R₅ is a hydrogen or a linear or branched alkyl group from C₁ to C₄; and

R* is the organic part derived from a primary or secondary fragrant alcohol R*OH.

3. The perfuming composition according to claim 1, wherein R₁ is an isopropyl group.

4. The perfuming composition according to claim 1, wherein the fragrant alcohol R*OH from which is derived from R* is geraniol, (E)-3,3-dimethyl-5-(2',2',3'-trimethyl-3'-cyclopenten-1'-yl)-4-penten-2-ol or phenethyol.

5. The perfuming composition according to claim 1, wherein the 2-benzoyl benzoate is geranyl 2-benzoyl benzoate, geranyl 2-(2'-isopropylbenzyl)benzoate, geranyl 2-(2',4'-diisopropylbenzoyl)benzoate or (E)-3,3,-dimethyl-5-(2',2',3'-trimethyl-3'-cyclopenten-1'-yl)-4-penten-1-yl or 2-(2',4'-diisoprobylbenzoyl)benzoate.

6. The perfuming composition according to claim 1, further comprising a hydrogen radical source which is a solvent selected from the group consisting of primary or secondary aliphatic alcohols, aromatic alcohols, diols and polyols, ketones, esters, alkyl-substituted aromatic compounds, ethers, aminoalcohols and linear and branched hydrocarbons, provided that said solvents contain a linear alkyl group higher than ethyl or a branched secondary alkyl group.

7. The perfuming composition according to claim 6, wherein the solvent is isopropanol, 1-dodecanol, 2-tridecenol, butanol or amyl alcohol.

8. The perfuming composition according to claim 1, wherein R* represents: a) a C₆ to C₁₂ linear or branched, saturated or unsaturated hydrocarbon radical; b) C₁₀ to C₁₆ saturated or unsaturated cycloaliphatic radical; or c) C₈ to C₁₂ substituted or unsubstituted aromatic radical.

9. The perfuming composition according to claim 1, wherein R* is derived from alcohols selected from the group consisting of: anisic alcohol, cinnamic alcohol, fenchylic alcohol, 9-decen-1-ol, phenethylol, citronellol, 3-methyl-5-phenyl-1-pentanol, 7-p-methan-1-ol, 3,7-dimethyl-2,6-octadien-1-ol, (Z)-3-hexen-1-ol, 1-hexanol, 2-hexanol, 5-ethyl-2-nonanol, 2,6-nonadien-1-ol, borneol, 1-octen-3-ol, cyclomethyl citronellol, decanol, dihydroeugenol, 8-p-menthol, 3,7-dimethyl-1-octanol, dodecanol, eugenol, isoeugenol, 2-methoxy-4-propyl-1-cyclohexanol, (E)-3,3-dimethyl-5-(2',2',3'-trimethyl-3'-cyclopenten-1'yl)-4-penten-2-ol, and 1-(2',2',3',6'-tetramethyl-cyclohex-1-yl-3-hexanol.

10. The perfuming composition according to claim 1, wherein the fragrant alcohol R*OH from which R* is derived is geraniol.

11. A perfumed article containing at least one of the perfuming compositions according to claim 1.

12. The perfumed article according to claim 11, in the form of a perfume or a cologne, a bath or shower gel, a shampoo, a hair spray or other hair-care product, a cosmetic preparation, a body deodorant, a solid or liquid air-freshener, a detergent or a fabric softener, a household cleaner, an all-purpose cleaner, a window cleaner, or a furniture polish.

* * * * *

UNITED STATES PATENT AND TRADEMARK OFFICE
CERTIFICATE OF CORRECTION

PATENT NO. : 6,369,026 B1
DATED : April 9, 2002
INVENTOR(S) : Pika et al.

It is certified that error appears in the above-identified patent and that said Letters Patent is hereby corrected as shown below:

<u>Column 28,</u>
Line 17, please change "1-(2',2',3',6'-tetramethyl-cyclohex-1-yl-3-" to
-- 1-(2',2',3',6'-tetramethyl-cyclohex-1-yl)-3- --.

Signed and Sealed this

Seventeenth Day of June, 2003

JAMES E. ROGAN
*Director of the United States Patent and Trademark Office*